(12) United States Patent
Dhooge et al.

(10) Patent No.: US 10,517,983 B2
(45) Date of Patent: Dec. 31, 2019

(54) HYGIENE ARTICLE COMPRISING AN EFFECTIVE ODOUR CONTROL SYSTEM

(71) Applicant: ONTEX BVBA, Buggenhout (BE)

(72) Inventors: Lieven Dhooge, Eeklo (BE); Karen Roets, De Pinte (BE)

(73) Assignee: ONTEX BVBA, Buggenhout (BE)

( * ) Notice: Subject to any disclaimer, the term of this patent is extended or adjusted under 35 U.S.C. 154(b) by 206 days.

(21) Appl. No.: 15/123,429

(22) PCT Filed: Mar. 3, 2015

(86) PCT No.: PCT/EP2015/054438
§ 371 (c)(1),
(2) Date: Sep. 2, 2016

(87) PCT Pub. No.: WO2015/132267
PCT Pub. Date: Sep. 11, 2015

(65) Prior Publication Data
US 2017/0216481 A1 Aug. 3, 2017

(30) Foreign Application Priority Data

Mar. 3, 2014 (EP) .................................. 14157525
Nov. 7, 2014 (BE) .................................. 2014/5059

(51) Int. Cl.
*A61L 15/46* (2006.01)
*A61L 15/20* (2006.01)
*A61F 13/84* (2006.01)
*A61L 15/40* (2006.01)

(52) U.S. Cl.
CPC .......... *A61L 15/46* (2013.01); *A61F 13/8405* (2013.01); *A61L 15/20* (2013.01); *A61L 15/40* (2013.01); *A61F 2013/8414* (2013.01); *A61F 2013/8426* (2013.01); *A61L 2300/404* (2013.01)

(58) Field of Classification Search
CPC .......... A61F 13/8405; A61F 2013/8414; A61F 2013/8408; A61F 2013/8417; A61F 2013/8426; A61F 2013/8438; A61F 2013/8435
See application file for complete search history.

(56) References Cited

U.S. PATENT DOCUMENTS

| | | | |
|---|---|---|---|
| 5,429,628 A * | 7/1995 | Trinh ................. | A61K 8/0208 604/359 |
| 5,591,146 A * | 1/1997 | Hasse ................. | A61F 13/5611 604/359 |
| 6,703,536 B2 * | 3/2004 | Roe ..................... | A61L 15/46 604/359 |
| 7,473,817 B1 * | 1/2009 | Tanaka ................ | A61F 13/8405 442/121 |
| 2003/0208173 A1 * | 11/2003 | Lagerstedt-Eidrup ..... | A61F 13/8405 604/367 |
| 2004/0024374 A1 * | 2/2004 | Hjorth ................. | A61F 13/84 604/367 |
| 2005/0152953 A1 * | 7/2005 | Wild ................... | A61K 8/0208 424/443 |
| 2006/0171971 A1 * | 8/2006 | Marsh ................. | A61K 8/0208 424/401 |
| 2007/0020342 A1 * | 1/2007 | Modak ................. | A61K 8/27 424/642 |
| 2008/0146986 A1 * | 6/2008 | Riga ................... | A61N 1/0436 604/20 |
| 2008/0300561 A1 * | 12/2008 | Stridfeldt ............ | A61F 13/8405 604/367 |
| 2009/0263342 A1 * | 10/2009 | Glenn, Jr. ............ | A61K 8/345 424/70.11 |
| 2010/0047303 A1 * | 2/2010 | Yhlen ................. | A61L 15/18 424/409 |
| 2010/0069861 A1 * | 3/2010 | Yao ................... | A61F 13/15804 604/360 |
| 2012/0226248 A1 * | 9/2012 | Caputi ................. | A61L 15/28 604/359 |
| 2013/0025764 A1 * | 1/2013 | Henderson ............. | A01N 25/10 156/60 |
| 2013/0295027 A1 * | 11/2013 | Saji ................... | A61K 8/27 424/56 |
| 2014/0169856 A1 * | 6/2014 | Doering ................. | A45D 40/00 401/55 |
| 2016/0184146 A1 * | 6/2016 | Tulk ................... | A61L 15/46 514/560 |

FOREIGN PATENT DOCUMENTS

| | | |
|---|---|---|
| CN | 101534764 A | 9/2009 |
| EP | 1759716 A1 | 3/2007 |
| EP | 2468309 A1 | 6/2012 |

(Continued)

OTHER PUBLICATIONS

Huggins, G.R. et. al., "Vaginal odors and secretions," Clin. Obstet. Gynecol. 24(2):355-77 (1981).
Decision to Grant in corresponding European App. No. 15707390.9, dated Jan. 17, 2019.
Decision to Grant in corresponding Australian App. No. 2015226197, dated Oct. 29, 2018.
Office Action in corresponding Australian App. No. 2015226197, dated Jul. 3, 2018.
Office Action in corresponding Chinese App. No. 201580020770.5, dated Dec. 4, 2018 (English Translation).

*Primary Examiner* — Susan S Su
(74) *Attorney, Agent, or Firm* — Vivicar Law, PLLC

(57) ABSTRACT

The present invention relates to a hygiene article comprising an effective odour control system, wherein essential oils, an organic zinc salt such a zinc ricinoleate, and preferably a chelating agent and/or a physical agent interact synergistically to reduce malodours of bodily fluids. The present invention is of particular importance to the field of hygiene products, in particular feminine hygiene absorbent articles (sanitary napkins, panty liners).

24 Claims, No Drawings

(56) References Cited

FOREIGN PATENT DOCUMENTS

| WO | WO 98/38868 A1 | 9/1998 |
| WO | 2008058565 A1 | 5/2008 |
| WO | WO 2008/058564 A1 | 5/2008 |
| WO | 2017089108 A1 | 6/2017 |

* cited by examiner

HYGIENE ARTICLE COMPRISING AN EFFECTIVE ODOUR CONTROL SYSTEM

CROSS-REFERENCE TO RELATED APPLICATIONS

This application is the U.S. National Phase under 35 U.S.C. § 371 of International Application PCT/EP2015/054438, filed Mar. 3, 2015, which claims priority to EP 14157525.8 filed Mar. 3, 2015 and BE2014/5059, filed Nov. 7, 2014.

TECHNICAL FIELD

The present invention relates to a hygiene article comprising an effective odour control system, wherein essential oils and/or the active ingredients thereof, an organic zinc salt such as zinc ricinoleate and a chelating agent interact synergistically to reduce malodours of bodily fluids. The present invention is of particular importance to the field of hygiene products, in particular feminine hygiene absorbent articles (sanitary napkins, panty liners).

BACKGROUND

A wide variety of disposable absorbent articles which are designed not only to be efficient in the absorption of body fluids such as urine, blood, menses and the like, but also to be sanitary and comfortable in-use, are known in literature. Disposable absorbent products of this type generally comprise a fluid-permeable topsheet material, an absorbent core (or a fluid storage layer), and a fluid-impermeable backsheet material. Various shapes, sizes and thicknesses of such articles have been explored in an attempt to make their use more comfortable and convenient.

Recently, research has been focused on the removal of unpleasant odours. Many body fluids have an unpleasant odour (or a malodour), or develop such an odour when in contact with air and/or bacteria for prolonged periods. Urine and/or other exudates absorbed into the absorbent article can be converted to ammonia by urease produced by micro-organisms present in the urogenital (vaginal, fecal, skin . . . ) flora. Among others, ammonia could become a source of unpleasant odours. Furthermore, typical malodours related to the use of hygiene absorbent articles include fatty acids, amines, sulphur containing compounds, ketones, aliphatic acids and aldehydes.

Many attempts have been made to prevent malodours to be perceived by the user of disposable absorbent articles. One approach is disclosed in EP2468309A1 in which cyclodextrin is complexed with a menthol family compound and an ionone in an absorbent article. In order for the cyclodextrin complex to effectively release the components of the cyclodextrin complex, the complex needs to come in contact with moisture. Also here, a problem with such an odour control system exists when incorporating a cyclodextrin complex in an absorbent article, because other components, such as the absorbent core and/or superabsorbent material, of the absorbent article have a strong affinity for bodily fluids. When an absorbent article comes in contact with bodily fluid, such as menses or urine, the cyclodextrin complex is thus in competition with the absorbent core and/or superabsorbent material for the moisture contained in the bodily fluid. This competition thereby reduces the amount of moisture available to contact the cyclodextrin complex and limits the effective action of the odour control system. Another disadvantage to this odour control system is that it only provides a way to mask the malodours and does not prevent/limit the formation of new malodours, for example produced by degradation of blood, urine and/or other exudates by micro-organisms.

EP2083873B1 discloses an absorbent article wherein an organic zinc salt such as zinc ricinoleate and an anti-microbial agent or alkali metal chloride or alkaline earth metal chloride interact to reduce malodours such as ammonia. Also here, disadvantages are linked to the proposed solution as the antibacterial agents used are from non-natural origin, which can cause safety issues.

Each of these approaches has its drawback. None of prior art has identified a disposable absorbent article to effectively suppress a multitude of different types of malodours from bodily fluids.

Therefore, an ongoing demand exists in the art for effective odour control systems in absorbent articles. In particular, it would be desirable to provide an odour control system which achieves efficient odour reduction.

The present invention aims to resolve at least some of the problems mentioned above.

The invention thereto aims to provide an improved hygienic article with an odour control system that is able to diminish the perception of all odours related to bodily excretions present on the hygiene article, with a focus on vaginal secretions, blood, sweat, urine, ammonia and others.

SUMMARY OF THE INVENTION

The present invention concerns a hygiene article, preferably a disposable absorbent article, in particular feminine hygiene absorbent articles such as sanitary napkins, panty liners, etc., or diapers such as baby diapers or adult incontinence diapers.

In a first aspect, the present invention is directed to a hygiene article comprising an odour control composition comprising an anti-microbial agent and an organic zinc salt, and preferably a chelating agent and/or a physical agent working according to the Zwaardemaker principle. Herein, the anti-microbial agent is selected from the group comprising essential oils and/or the active components thereof. Preferably the anti-microbial agent and the organic zinc salt, and, in a preferred embodiment, also the chelating agent and/or the physical agent, are provided in an odour control composition for preventing and/or suppressing malodours. Preferably the hygiene article comprises a layer, like a liquid absorbent core or an acquisition and distribution layer, which is provided with a mixture of said anti-microbial agent and said organic zinc salt and preferably said chelating agent and/or said physical agent. Surprisingly, it has been observed that this combination of an anti-microbial agent selected from the group comprising essential oils and/or the active components thereof and an organic zinc salt, and preferably a chelating agent and/or a physical agent, results in a combined odour control effect both on short term and on long term, which was not previously anticipated.

In a preferred embodiment, the anti-microbial agents, selected from the group comprising essential oils, comprise oils of the tea tree, cinnamon, citronella, artemisia, lemongrass, cedar, cloves, pine, bergamot, lemon, orange, thyme, cardamom and lavandino, and mixtures thereof and/or the active components preferably comprise thymol, citronellal, citronellol, estragol, geranyl acetate, eucalyptol, eugenol, linalool, linalyl acetate, terpineol, cinnamaldehyde, cinnamic acid, citral, dihydromyrcenol, rose oxide, cineol and cajeputene. One advantage of the invention is that the safety profile of essential oils and/or the active ingredients thereof is much superior to that of the majority of non-natural anti-microbial additives that are commonly used in odour control prior art hygiene article. The essential oils and/or the active ingredients thereof possess intrinsic odorous properties, allowing the composition thereof to have freshening or aromatic properties without the necessity to add an additional perfume.

In a preferred embodiment, organic zinc salts have proven to be effective against nitrogen containing malodorous molecules, sulphur containing malodours, aliphatic acids and aldehydes. Sulphur containing malodours and aliphatic acids are of particular interest for hygiene articles, namely feminine hygiene products, as they are great contributors to the overall offensive odour of used sanitary napkins and panty liners.

In a preferred embodiment, the hygiene article comprises a chelating agent which prevents malodours of being formed by slowing down the breakdown of the bodily exudates including urine, blood & blood components. The chelating agent makes sure that essential component(s) for degradation reactions such as iron-ions are made unavailable in the environment. Next to that, it is also known to reduce the growth rate of odour causing micro-organisms, e.g. *Proteus mirabilis*, a common bacteria that is part of the urogenital microflora and is urease positive, rapidly breaking down urea into ammonia.

In a preferred embodiment, the hygiene article comprises a physical agent working according to the Zwaardemaker principle, such as ionones, that are of particular interest in the invention because it is a class of compounds which are useful for reducing the perception of sulphur smells. Such sulphur based compounds are typically generated by the degradation of menstrual fluids and their control is particularly important in menstrual absorbent articles such as sanitary napkins or panty liners.

In a preferred embodiment, the hygiene article comprises a slow release system for slowly releasing said odour control composition.

In a second aspect, the present invention provides a method for manufacturing a hygiene article, preferably the hygiene article as described in this document, comprising the steps of providing a hygiene article comprising a topsheet, a backsheet and one or more layers positioned between said topsheet and said backsheet; and treating the article, one or more of layers, the topsheet and/or the backsheet with an odour control composition of an anti-microbial agent selected from the group comprising essential oils and/or active components of essential oils, and an organic zinc salt, and preferably a chelating agent and/or a physical agent, thereby providing said article with an odour control composition.

In a further aspect, the present invention provides another method for producing a hygiene article, preferably the hygiene article as described in this document, comprising the steps of treating a topsheet, a backsheet and/or one or more layers, suitable for use in a hygiene article, with an odour control composition of an anti-microbial agent selected from the group comprising essential oils and/or active components of essential oils, and an organic zinc salt, and preferably a chelating agent and/or a physical agent; and assembling a hygiene article comprising one or more layers positioned between a top sheet and a back sheet, at least one of said topsheet, backsheet or layers being treated with said odour control composition, thereby providing said article with an odour control composition.

In a further aspect, the present invention provides use of an anti-microbial agent comprising essential oils and/or active ingredients thereof and an organic zinc salt, and preferably a chelating agent and/or physical agent working according to the Zwaardemaker principle, as an odour control composition for a hygiene article.

In a preferred embodiment, the hygiene article with odour control composition provided by the invention is an absorbent article, more preferably a feminine hygiene absorbent article or a diaper, most preferably a sanitary napkin, panty liner or adult incontinence briefs. In a particularly preferred embodiment, said article comprises a liquid-absorbing core.

Other preferred embodiments are as specified in the dependent claims and further in this document.

The overall aim of the present invention is to offer an efficient and durable protection against bad odours during the use of an absorbent hygiene article, in particular a sanitary napkin or panty liner.

Typical malodours related to used hygiene articles include fatty acids, ammonia, amines, sulphur containing compounds, ketones, aliphatic acids and aldehydes (see e.g. George R. Huggins et al., "Vaginal Odors and Secretions", Clinical Obstetrics and Gynaecology, Vol 24, No. 2, June 1981, Harper & Row, Publishers, Inc.). They are present as natural ingredients of bodily fluids or result from degradation processes of natural ingredients such as urea or blood, which are frequently assisted by micro-organisms occurring in the urogenital flora (vaginal, fecal, skin . . . flora) and which are present on the absorbent products during use.

Bodily fluids that are likely to be present in hygiene articles are urine, menses (including blood and blood components), vaginal secretions and sweat.

More in particular, odorous components may comprise:
Aliphatic acids, such as propionic acid, butyric acid, isovaleric acid, valeric acid, lactic acid . . . .
Sulphur containing compounds, such as hydrogen sulfide, methyl mercaptane, dimethyl sulfide, dimethyl disulfide . . . .
Nitrogen containing compounds, such as pyrrole, indole, trimethyl amine, ammonia, 2-piperidone . . . .
Aldehydes, such as acetaldehyde, propionaldehyde, butyraldehyde, valeraldehyde, isovaleraldehyde . . . .
Ketones, such as 2-butanone, 2-pentanone, 4-heptanone, 2-Methyl-5-(1-methylethenyl)-2-cyclohexenone, methylisobutylketone . . . .
Fatty acids, such as 3-methyl-2-hexenoic acid, 3-hydroxy-3-methyl-hexanoic acid . . . .

To offer an efficient and durable protection against bad odours, especially for sanitary napkins or panty liners, an effective odour control needs to be present towards sulphur containing malodours (hydrogen sulfide, methyl mercaptane . . . ) and aliphatic acids (lactic acid, butyric acid . . . ). However, Other types of malodours are also addressed by the present invention.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:
"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, feminine hygiene absorbent articles such as sanitary napkins or panty liners, adult incontinence briefs, training pants, diaper holders and liners.

"Diaper" refers to an absorbent article generally worn by infants and incontinent persons about the lower torso.

"Disposable" is used herein to describe articles that are generally not intended to be laundered or otherwise restored or reused (i.e. they are intended to be discarded after a single use and, preferably, to be recycled, composted or otherwise disposed of in an environmentally compatible manner).

The absorbent article of the present invention preferably comprises a liquid permeable top sheet, a liquid impermeable back sheet, and an absorbent core disposed between the top sheet and the back sheet. Optionally, the absorbent article can comprise of one or more acquisition and distribution layers positioned between the top sheet and back sheet, more preferably between the top sheet and an absorbent core or layer, even more preferably directly under or near the top sheet.

The term "top sheet" refers to a liquid permeable material sheet forming the inner cover of the absorbent article and which in use is placed in direct contact with the skin of the wearer. The top sheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. Further examples of top sheet materials are porous foams, apertured plastic films, laminates of nonwoven materials and apertured plastic films etc. The materials suited as top sheet materials should be soft and non-irritating to the skin and be readily penetrated by bodily fluid, e.g. urine or menstrual fluid. The inner coversheet may further be different in different parts of the absorbent article. The "back sheet" refers to a material forming the outer cover of the absorbent article. The back sheet may be the same or different in different parts of the absorbent article. At least in the area of the absorbent medium, the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

"Absorbent medium" or "absorbent core" is the absorbent structure disposed between the top sheet and the back sheet of the absorbent article in at least the crotch region thereof. It comprises absorbent material which can be of any conventional kind. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

"Acquisition and distribution layer" or "ADL", refers to a sub-layer which preferably is a nonwoven wicking layer under the topsheet (or face fabric) of an absorbent product, which speeds up the transport and improves distribution of fluids throughout the absorbent core.

Preferably, the hygiene article comprises an absorbent core which comprises an odour control composition according to the present invention.

"Anti-microbial agent" refers to a compound which is able to kill micro-organisms that exist in the urogenital region of humans, like bacteria (such as ammonia-generating bacteria), or fungi, e.g. yeasts such as *Candida albicans*, or to suppress the growth of said bacteria or fungi.

"Chelating agent" refers to a compound that binds at multiple points in a coordination complex to a solubilized (metal) ion, resulting in a physiologically stable chelate complex with a variety of metal ions. Chelating agents can be chosen from the non-limiting list of 2-Amino ethyl phosphonic acid (EPNA), Dimethyl methyl phosphonate (DMMP), 1-Hydroxy ethylidine-1,1-diphosphonic acid (HEDP), Aminotris (methylene phosphonic acid) (TMPA), Ethylenediaminetetra (methylene phosphonic acid) (EDTMP), Tetrametilendiaminotetra (methylene phosphonic acid) (TDTMP), Hexametilendiaminotetra (methylene phosphonic acid) (HDTMP), Diethylenetriaminepenta (methylene phosphonic acid) (DTPMP), Ethylenediaminetetraacetic acid (EDTA), Phosphonobutane tricarboxylic acid (PBTC), N-(phosphonomethyl) iminodiacetic acid (PMIDA), 2-Carboxy ethyl phosphonic acid (CEPA), 2-Hydroxy phosphono carboxylic acid (HPCA), Amino-tris (methylene phosphonic acid) (AMP), Sodium tripolyphosphate (STPP), Hydroxyethyl ethylene diaminne triacetic acid (HEDTA), Dihydroxy ethyl ethylene diamine diacetic acid, Diehylene triamine pentaacetic acid (DTPA), Triethylene tetramine hexaacetic acid (TTHA), Ethylene diamine di-hydroxyphenyl acetic acid (EDDHA), Ethylene diamine di-(2-hydroxy-5-sulphophenylacetic) acid (EDDHSA), Ethylene diamine di-hydroxy-methylphenylacetic acid (EDDHMA), Ethylene diamine di-(5-carboxy-2-hydroxyphenyl) acid (EDDCHA), Calcium disodium ethylene diamine tetraacetate (CaNa2EDTA), Nitrile triacetic acid (NTA), Propylene diamine tetraacetic acid (PDTA), Polyflavonoides, Sulfonates, Dimercaptosuccinic acid, Fulvic and humic acid, Lignosulphonic acid, Gluconic acid, Amino acids, Polysaccharides, Polyols, Glutamic acid, Citric, tartaric, ascorbic, malic, fumaric, lactic acid or combinations thereof.

The term "Essential oils and/or active components thereof" is used herein to describe oils or extracts distilled or expressed from plants and active components of these oils. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, [beta]-pinene, limonene), orange (limonene, citral), anise (anethole, safrol), clove (eugenol, eugenyl acetate, caryophyllene), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene); wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), cardamom (eucalyptol, cineol) and cedar leaf ([alpha]-thujone, [beta]-thujone, fenchone). Essential oils are widely used in perfumery and as flavorings, medicine and solvents. Essential oils from the present invention are also used in hygiene articles such as sanitary napkins, panty liners. Essential oils, their composition and production, are described in detail in Kirk-Othmer Encyclopedia of Chemical Technology, 4th Edition and in The Merck Index, 13th Edition. Preferably, said essential oils are hydrophobic and/or comprise a volatile active component.

"Organic zinc salts" refers to zinc salts of organic carboxylic acids having 2 to 30 carbon atoms, in particular 12 to 24 carbon atoms are preferably used. The carboxylic acid group may be attached to aliphatic, aliphatic-aromatic, aromatic aliphatic, alicyclic or aromatic residues, wherein the aliphatic chain or the alicyclic ring(s) may be unsaturated and are optionally substituted for instance by hydroxyl or C1 to C4 alkyl. These salts include zinc acetate, zinc lactate, zinc ricinoleate and zinc abietate. More preferably, the zinc salt is the zinc salt of an unsaturated hydroxylated fatty acid having 8 to 18 carbon atoms. Although there is no specific restriction regarding the number of unsaturated double bonds or hydroxy groups, those fatty acids having one or two unsaturated double bonds and one or two hydroxyl groups seem to be preferred. The most preferred embodiment is zinc ricinoleate. Zinc ricinoleate is the zinc salt of ricinoleic acid, a major fatty acid found in castor oil. It is used in many deodorants as an odour-neutralising agent.

The term "physical agent working according to the Zwaardemaker principle" refers to a fragrance compound that binds preferentially at some or all of the nose receptor sites of the human body that certain malodour compounds bind to. This means that if both compounds are present in the nasal cavity, there is a reduced ability for the malodour to be perceived. Ionones, such as α-ionones, β-ionones or γ-ionones, are examples of such physical agents, as these components show an effective "masking" effect towards sulphur containing malodours by making the nose receptors less effective in detecting the malodours when ionone(s) are present. Preferably, the ionones used are selected from the list of 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)4-penten-3-one, (E)-4-(2,2-dimethyl-6-methylidenecyclohexyl)but-3-en-2-one; or a mixture thereof.

The inventors have found a way to provide an improved hygiene article with odour control.

In particular, the present invention provides in a first aspect a hygiene article comprising an odour control composition comprising an anti-microbial agent selected from the group comprising essential oils and/or an active component thereof and an organic zinc salt. The present invention also provides a hygiene article comprising an odour control composition comprising a chelating agent and/or a physical agent working according to the Zwaardemaker principle, such as ionones. The present invention further provides a hygiene article comprising an odour control composition comprising an anti-microbial agent selected from the group comprising essential oils and/or an active component thereof and an organic zinc salt, and a chelating agent and/or a physical agent working according to the Zwaardemaker principle, such as ionones.

In the present invention, one or more essential oils in an effective amount are used to provide two functions: inhibit the growth of odour creating microbes and emit a pleasant aroma. Preferably, the anti-microbial agents selected from the group comprising essential oils comprise oils of the tea tree, cinnamon, citronella, artemisia, lemongrass, cedar, cloves, pine, bergamot, lemon, orange, thyme, cardamom and lavandino, and mixtures thereof and their active components are preferably thymol, citronellal, citronellol, estragol, geranyl acetate, eucalyptol, eugenol, linalool, linalyl acetate, terpineol, cinnamaldehyde, cinnamic acid, citral, dihydromyrcenol, rose oxide, cineol and cajeputene.

Anti-microbial agents selected from the group comprising essential oils for use in the present invention are compounds which are of natural origin and are skin-friendly, which is supported by extensive dermatological testing with gynecological check. It needs to be borne in mind that the skin area being in contact with absorbent products such as diaper, panty diaper, sanitary napkin or incontinence device is sensitive and delicate. The safety profile of essential oils and/or the active ingredients thereof is much superior to that of the majority of non-natural anti-microbial additives. In fact, the majority of essential oils of interest are accepted as aromatic agents, natural repellants, food additives or natural preservatives for human or animal consumption. Furthermore, the hygiene article is an environmentally friendly product that has the right features in odour control and safety.

Known odour control systems from the prior art are using for example, organic poly(acid) components such as benzoic acid, sorbic acid, tartaric acid or citric acid that are of non-natural origin as mentioned in EP2083873B1.

One additional advantage to use essential oils and/or the active ingredients in a hygiene article is that the essential oils and/or the active ingredients thereof possess intrinsic odorous properties, whereby they provide or enhance the smell of the odour control system, allowing the composition thereof to have freshening or aromatic properties without the necessity to add an additional perfume.

The amount of malodours that is still formed or present (some bodily fluids have a scent of their own, for example lactic acid present in vaginal secretions) in the absorbent article are actively neutralized. Organic zinc salt, which is a chemical neutralizer, has proven to be effective against nitrogen containing malodorous molecules such as ammonia and indole, sulphur containing malodours such as hydrogen sulfide, methyl mercaptane, dimethyl sulfide, dimethyl disulfide, etc., aliphatic acids such as lactic acid and butyric acid, and aldehydes such as acetaldehyde and butylaldehyde. Sulphur containing malodours and aliphatic acids are of particular interest for hygiene articles, namely feminine hygiene products, as they are great contributors to the overall offensive odour of used sanitary napkins and panty liners. Known odour control systems from the prior art are targeting primarily the prevention and neutralization of nitrogen containing malodours.

In a preferred embodiment, said odour control composition comprises a chelating agent. The chelating agent prevents malodours of being formed by slowing down the breakdown of blood and blood components. The chelating agent makes sure that essential component(s) for degradation reactions (for example the iron-ions) are made unavailable in the environment. Next to that, it is also known to reduce the growth rate of odour causing micro-organisms, e.g. *Proteus mirabilis*, a common bacteria that is part of the urogenital microflora and is urease positive, rapidly breaking down urea into ammonia.

In a preferred embodiment, said odour control composition comprises a physical agent working according to the Zwaardemaker principle, preferably ionones. Ionones are of particular interest in the invention because it is a class of compounds which are useful for reducing the perception of odours; in particular, these compounds are useful in the context of hygiene articles because ionones block the perception of sulphur smells by making the nose receptors less effective in detecting the malodours when ionone(s) are present. Malodourant sulphur based compounds are typically generated by the degradation of menstrual fluids and their control is particularly important in menstrual absorbent articles such as sanitary napkins or panty liners. Suitable ionones include, for example, 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)4-penten-3-one, (E)-4-(2,2-dimethyl-6-methylidenecyclohexyl)but-3-en-2-one; or a mixture thereof.

In a preferred embodiment, the organic zinc salt is or comprises zinc ricinoleate. Zinc ricinoleate is a zinc salt of ricinoleic acid, which can be derived from zinc and a purified fatty acid from castor seed oil, a vegetable oil obtained from the seeds of the *Ricinus communis* plant. Zinc ricinoleate has proven to be particularly effective against nitrogen containing malodorous molecules such as ammonia and indole, sulphur containing malodours such as hydrogen sulfide, methyl mercaptane, dimethyl sulfide, dimethyl disulfide, etc., aliphatic acids such as lactic acid and butyric acid, and aldehydes such as acetaldehyde and butylaldehyde.

In a preferred embodiment, said odour control composition comprises a chelating agent. A chelating agent binds at multiple points in a coordination complex to a solubilized (metal) ion, resulting in a physiologically stable chelate complex with a variety of metal ions. In this way, the chelator "protects" the metal ions and they are no longer available to enter in any other reaction, for example in the metabolism of a micro-organism, with components present in the solution. In particular, for this present invention, the chelators help in preventing the formation of malodours. One of the main components in blood, which is an important part of the bodily exudates captured by sanitary napkins or panty liners, is hemoglobin (in the red blood cells), which contains 4 heem groups, each with a Fe(II+) ion in the center. These Fe-ions can take part in numerous degradation processes. By keeping the Fe-ions unavailable by adding chelating agents, the degradation process of blood can be slowed down. Hence, an advantage of the present invention is that less malodorous components can be formed by the breakdown of blood, in particular in menses, in feminine absorbent articles. Such malodorous components issued from blood breakdown can be ammonia, hydrogen sulfide and ketones such as 1-octen-3-one, which are reduced in quantity when chelating agents are used. Furthermore, chelators could slow down the breakdown of ureum, present in urine. The chelating agents can be chosen from the non-limiting list of 2-Amino ethyl phosphonic acid (EPNA), Dimethyl methyl phosphonate (DMMP), 1-Hydroxy ethylidine-1,1-diphosphonic acid (HEDP), Aminotris (methylene phosphonic acid) (TMPA), Ethylenediaminetetra (methylene phosphonic acid) (EDTMP), Tetrametilendiaminotetra (methylene phosphonic acid) (TDTMP), Hexametilendiaminotetra (methylene phosphonic acid) (HDTMP), Diethylenetriaminepenta (methylene phosphonic acid) (DTPMP), Ethylenediaminetetraacetic acid (EDTA), Phosphonobutane tricarboxylic acid (PBTC), N-(phosphonomethyl) iminodiacetic acid (PMIDA), 2-Carboxy ethyl phosphonic acid (CEPA), 2-Hydroxy phosphono carboxylic acid (HPCA), Amino-tris (methylene phosphonic acid) (AMP), Sodium tripolyphosphate (STPP), Hydroxyethyl ethylene diaminne triacetic acid (HEDTA), Dihydroxy ethyl ethylene diamine diacetic acid, Diehylene triamine pentaacetic acid (DTPA), Triethylene tetramine hexaacetic acid (TTHA), Ethylene diamine di-hydroxyphenyl acetic acid (EDDHA), Ethylene diamine di-(2-hydroxy-5-sulphophenylacetic) acid (EDDHSA), Ethylene diamine di-hydroxy-methylphenylacetic acid (EDDHMA), Ethylene diamine di-(5-carboxy-2-hydroxyphenyl) acid (EDDCHA), Calcium disodium ethylene diamine tetraacetate (CaNa2EDTA), Nitrile triacetic acid (NTA), Propylene diamine tetraacetic acid (PDTA), Polyflavonoides, Sulfonates, Dimercaptosuccinic acid, Fulvic and humic acid, Lignosulphonic acid, Gluconic acid, Amino acids, Polysaccharides, Polyols, Glutamic acid, Citric, tartaric, ascorbic, malic, fumaric, lactic acid or combinations thereof.

In a preferred embodiment, the combination of the antimicrobial agent, the organic zinc salt, the chelating agent and the physical agent results in a combined effect in terms of odour control. Indeed this combination gives more odour reduction than the odour reduction associated to the use of one of these agents alone at the same total level (either the anti-microbial agent alone or the organic zinc salt alone or the chelating agents alone or the physical agent alone) in an absorbent article coming into contact with bodily fluids. Actually the combination of the anti-microbial agent with an organic zinc salt, a physical agent and with a chelating agent in an absorbent article herein allows to combine odour control mechanisms by which the malodour detection is synergistically reduced or even prevented as well as odour control over a very broad odour spectrum. It is only by achieving an anti-microbial, chemical, physical and chelation action at the same time that the most optimal odour control can be achieved. Whereas the individual components of the odour control composition each provide a way to reduce the perception of malodours, it is the combination of the components which provides a synergistically-effective composition that eliminates the perception of malodours, and/or prevent the formation of such malodours while simultaneously refraining from reduction of the perception of pleasant fragrance aromas emanating from the same source or from the proximity of said source, in particular in the case of malodours arising from blood, urine, vaginal secretions, etc.

As the selected active components are highly efficient, only a low amount is needed to reach the desired level of odour control in an absorbent article and more particular in feminine absorbent articles and this for a sufficient period in time. The active odour control proves to be efficient and durable in time.

A further advantage associated with the hygiene article of the present invention is that the odour-controlled hygiene article delivers a better feeling and more acceptable cleanness level for the person wearing them. Users expect not only that the use of the hygiene article is not seen, but also not smelled. As fresh smell is also linked to a feeling of cleanness, the need for hygiene articles including an active odour control system that is effective during the use of the hygiene article, is becoming more compulsory. In a first attempt to overcome malodours in hygiene articles, fragrances are added to the product. However, this does not offer a durable solution for the problem of malodours. During use, the amount of malodours is only rising and the addition of the fragrance cannot prevent this, thereby the masking effect becomes inefficient.

In the present invention, the hygiene article is preferably disposable after a single use.

In a preferred embodiment, said odour control composition is provided in a slow-release system, such as an encapsulation system.

In a preferred embodiment, the hygiene article is obtained by treating a topsheet, a backsheet and/or a layer positioned between the topsheet and the backsheet of the hygiene article with a mixed solution of the anti-microbial agent and the organic zinc salt and/or the chelating agent and/or the physical agent.

The present invention provides in a second aspect a method for manufacturing a hygiene article, preferably the hygiene article as described in this document, comprising the steps of providing (a) hygiene article comprising a topsheet, a backsheet and one or more layers positioned between said topsheet and said backsheet; and (b) treating the article, one or more of layers, the topsheet and/or the backsheet with an odour control composition of an anti-microbial agent selected from the group comprising essential oils and/or active components of essential oils, and an organic zinc salt, and preferably a chelating agent and/or a physical agent. Preferably the article and/or the layers are treated by spraying, impregnating and/or dipping the article and/or layer with said composition. In case spraying is used to treat the article and/or layer, either one or both sides of the article and/or layer can be sprayed. A layer can for example be, but is not limited to, a liquid absorbent core or an acquisition and distribution layer or both.

The present invention provides in an alternative aspect a method for manufacturing a hygiene article, preferably the hygiene article as described in this document, comprising the steps of (a) treating a topsheet, a backsheet and/or one or more layers, suitable for use in a hygiene article, with an odour control composition of an anti-microbial agent selected from the group comprising essential oils and/or active components of essential oils, and an organic zinc salt, and preferably a chelating agent and/or a physical agent; and (b) assembling a hygiene article comprising one or more layers positioned between a top sheet and a back sheet, at least one of said topsheet, backsheet or layers being treated with said odour control composition. Preferably the layers are treated by spraying, impregnating and/or dipping the layer with said mixed solution. In case spraying is used to treat the layer, either one or both sides of the layer can be sprayed. A layer can for example be, but is not limited to, a liquid absorbent core or an acquisition and distribution layer or both.

The hygiene article can, in other words, first be partially or completely assembled with the different components of which it is comprised and then be treated with the composition, or first one or more of the components can be treated with the composition and then the hygiene article can be assembled.

The mixed solution can also be treated on components comprised by the layer. For instance, it is conceivable to treat pulp fibers, to be used in an absorbent core, with the mixed solution prior to or during their mixture with superabsorbent polymer particles (SAP), to be used in the same absorbent core.

Further, the method comprises the steps of providing an anti-microbial agent, providing an organic zinc salt, optionally mixing said anti-microbial agent and said organic zinc salt and applying said anti-microbial agent and said organic zinc salt to a hygiene article, preferably to a layer comprised by the hygienic article. The anti-microbial agent comprises essential oils or active components thereof. Further, the anti-microbial agent and the organic zinc salt can be provided and/or applied separately or can be provided in a mixture or composition, preferably a liquid mixture in order to be applied to the hygiene article.

Further, the method comprises the steps of:
a. providing a chelating agent;
b. optionally mixing said chelating agent with the anti-microbial agent and/or organic zinc salt;
c. applying said chelating agent to said hygiene article.

Further, the method comprises the steps of:
a. providing a physical agent;
d. optionally mixing said physical agent with said anti-microbial agent and/or organic zinc salt and/or said chelating agent;
e. applying said physical agent to said hygiene article.

In a further aspect, the present invention provides the use of an anti-microbial agent comprising essential oils and/or active ingredients thereof and an organic zinc salt, and/or a chelating agent, and/or a physical agent as an odour control composition for a hygiene article.

In a preferred embodiment, the hygiene article comprises a liquid absorbent core, preferably whereby the article is a sanitary napkin, panty liner or adult incontinence briefs.

Although the present invention has been described with reference to preferred embodiments thereof, many modifications and alternations may be made by a person having ordinary skill in the art without departing from the scope of this invention which is defined by the appended claims.

EXAMPLE 1

Products used for testing are panty liners, produced on a commercial line. Products are composed out of a topsheet, with softsides on the longitudinal edges, an absorption and distribution layer, a core composed out of a folded airlaid layer, which is overlapping on the longitudinal edges, said core containing superabsorbent particles which are adhered to the inside part of the folded airlaid layer by use of spirals of a hotmelt, an impermeable backsheet layer, hotmelt applied to the garment side of the backsheet, which is protected of fouling by a silicon paper. The core is composed out of airlaid and superabsorbent material. Airlaid used was 0.59 g Buckeye airlaid (Vicell® 6721 DS W 50) and superabsorbent material used was 0.2 g Sumitomo SAP (SA60B). To the product, 0.036 mL of the odour control solution (composition: Table 1) was added by dripping the solution on the upper surface of the product, in the center. Subsequently, a mixture of contaminants (composition: Table 2), typical for bodily exudates captured by feminine hygiene products, is added to the product, in the center.

TABLE 1

Composition of odour control solution

| | |
|---|---|
| Organic zinc salt | Zinc ricinoleate |
| Chelating agent | EDTA |
| Physical agent | B-ionone |
| Essential oils as anti-microbial agent | Lemon oil Orange oil Thyme oil |

TABLE 2

Composition of contaminants

| Components | By weight (g) |
|---|---|
| Blood (non menstrual) | 2.4 |
| Synthetic urine | 0.5 |
| Synthetic sweat | 0.1 |

One treated product as described above is placed in a closed glass container (volume: 750 mL). An untreated product, containing only the contaminants and not the odour control solution, is placed in a same type of container. During the 24 h period of testing, the glass containers are kept at room temperature (21° C.±3° C.).

An olfactive evaluation of the samples is carried out by a group of highly trained experts, perfumers and evaluators, with more than 15 years of experience in the creation, evaluation and selection of fragrances. The odour neutralizing power of the present invention is determined by comparing the treated and untreated product after 0 h, 1 h, 3 h, 6 h, 12 h and 24 h of addition of odour control solution and/or contaminants to the products. Scoring is according to values mentioned in Table 3. Results of the olfactive evaluation can be found in Table 4.

TABLE 3

Odour neutralization evaluation scale

| Score | Odour neutralisation |
|---|---|
| 1 | No elimination of the bad odour = we perceive enough the bad odour |
| 2 | Something of the bad odour is eliminated = we continue perceiving the bad odour |
| 3 | Normal elimination of the bad odour = we perceive a little the bad odour & we perceive a little the fragrance |
| 4 | Complete elimination of the bad odour = we perceive the fragrance |

TABLE 4

Olfactive analysis

| Duration | Odour neutralization score |
|---|---|
| 0 h | 3.00 |
| 1 h | 3.50 |
| 3 h | 3.50 |
| 6 h | 3.50 |
| 12 h | 3.80 |
| 24 h | 3.80 |

The above results show that the combined use of the anti-microbial agent, the organic zinc salt and the chelating agent lead to the desired level of odour control in an absorbent article and more particular in feminine absorbent articles and this for a sufficient period in time. The active odour control proves to be efficient and durable in time as well.

EXAMPLE 2

The products used for testing, panty liners, are the same as described in Example 1. Both a treated, including the odour control solution as described in Table 1, as an untreated product, without the odour control solution, are subjected to an in-use test, executed by the external company Eurofins Marketing Research, Rue Pierre Adolphe Bobierre, 44300 Nantes, France. The treated product is produced on a commercial line, meaning that the odour control solution is added during the production process.

The ultimate aim is to have a panty liner that offers a good and durable protection against bad odours. For this, the odour control solution needs to be present next to the bodily exudates captured by the product. In an optimal use of the product, the bodily exudates enter the product in the center of the topsheet, go through the topsheet and reach the acquisition and distribution layer. Finally the exudates are captured by the core where they are absorbed by the SAP particles and cellulose fibers of the airlaid layer and remain for the duration of the use of the panty liner. The odour control solution is preferably present next to the bodily exudates once captured by the core, as this is the most likely place for bad odour formation. This can be achieved by placement of the odour control solution between acquisition and distribution layer and the core. The exudates are very likely to pass this location and take up the odour control solution, resulting in a mix of bodily exudates and odour control solution absorbed in the core. Placement of the odour control solution in the core can also be considered, but special attention will be needed not to activate the SAP particles.

The odour control solution is continuously added to the airlaid G-core, in the center, on the user-facing side. Treated area is 130 mm±3 mm long and 15 mm±3 mm wide. Application is done by spraying. The odour control solution is sprayed onto the airlaid using a spray head with two nozzles, with a pressure of ±0.4 bar.

Results of the in-use test confirm the efficacy of the odour control solution. Overall, the consumers separate the treated and untreated products, based on the fact that the treated products offer a significantly better protection against bad odours. The ultimate aim is reached to have a panty liner that offers both a good and durable protection against bad odours.

What is claimed is:

1. A hygiene article comprising an odour control composition for urine, menses, blood and blood components, vaginal secretions and sweat, the hygiene article comprising a liquid permeable topsheet, a liquid impermeable backsheet and at least one layer disposed between said liquid permeable topsheet and said liquid impermeable backsheet, wherein the at least one layer comprises a liquid absorbent core, and wherein said odour control composition consists essentially of:
    an organic zinc salt; and
    an anti-microbial agent comprising essential oil of thyme or thymol.

2. The hygiene article according to claim 1, comprising one or more acquisition and distribution layers positioned between said liquid permeable topsheet and said liquid absorbent core.

3. The hygiene article according to claim 2, wherein said odour control composition is positioned between the topsheet and the backsheet, and is contained within the liquid absorbent core, one or more of the acquisition and distribution layers or a combination thereof.

4. The hygiene article according to claim 1, wherein said organic zinc salt is selected from zinc salts of carboxylic acids having 2 to 30 carbon atoms.

5. The hygiene article of claim 4, wherein the carboxylic acid is an unsaturated hydroxylated fatty acid having 8 to 18 carbon atoms.

6. The hygiene article of claim 4, wherein said zinc salt comprises zinc ricinoleate.

7. The hygiene article according to claim 1, obtained by treating a topsheet, a backsheet, at least one layer disposed between the topsheet and the backsheet of the hygiene article, or a combination thereof with said odour control composition.

8. Method for manufacturing the hygiene article according to claim 1, comprising the steps of:
    a. providing a hygiene article comprising a liquid permeable topsheet, a liquid impermeable backsheet and at least one layer disposed between said liquid permeable topsheet and said liquid impermeable backsheet;
    b. treating the at least one layer, the liquid permeable topsheet, the liquid impermeable backsheet, or a combination thereof with an odour control composition consisting essentially of:
        an organic zinc salt; and
        an anti-microbial agent comprising essential oil of thyme or thymol.

9. Method for manufacturing the hygiene article according to claim 1, comprising the steps of:
    a. treating a liquid permeable topsheet, a liquid impermeable backsheet, at least one layer, suitable for use in a hygiene article, or combinations thereof with an odour control composition consisting essentially of:
        an organic zinc salt; and
        an anti-microbial agent comprising essential oil of thyme or thymol; and
    b. assembling the hygiene article by disposing the at least one layer between said liquid permeable topsheet and said liquid impermeable backsheet.

10. A method of controlling odour comprising administering the hygiene article of claim 1.

11. The method of claim 10, wherein the odor is caused by urine, menses, blood, blood components, vaginal secretions or sweat or a combination thereof.

12. A hygiene article comprising an odour control composition for urine, menses, blood and blood components, vaginal secretions and sweat, the hygiene article comprising a liquid permeable topsheet, a liquid impermeable backsheet and at least one layer disposed between said liquid permeable topsheet and said liquid impermeable backsheet, wherein the at least one layer comprises a liquid absorbent core, and wherein said odour control composition consists essentially of:
    an organic zinc salt;
    an anti-microbial agent comprising essential oil of thyme or thymol; and
    a chelating agent, a physical agent, or a combination thereof.

13. The hygiene article according to claim 12, comprising one or more acquisition and distribution layers positioned between said liquid permeable topsheet and said liquid absorbent core.

14. The hygiene article according to claim 12, wherein said odour control composition is positioned between the topsheet and the backsheet, and is contained within the liquid absorbent core, one or more of the acquisition and distribution layers, or a combination thereof.

15. The hygiene article according to claim 12, wherein said organic zinc salt is selected from zinc salts of carboxylic acids having 2 to 30 carbon atoms.

16. The hygiene article of claim 15, wherein the carboxylic acid is an unsaturated hydroxylated fatty acid having 8 to 18 carbon atoms.

17. The hygiene article of claim 15, wherein said zinc salt comprises zinc ricinoleate.

18. The hygiene article according to claim 12, wherein said chelating agent is selected from the group consisting of 2-Amino ethyl phosphonic acid (EPNA), Dimethyl methyl phosphonate (DMMP), 1-Hydroxy ethylidine-1,1-diphosphonic acid (HEDP), Aminotris (methylene phosphonic acid) (TMPA), Ethylenediaminetetra (methylene phosphonic acid) (EDTMP), Tetrametilendiaminotetra (methylene phosphonic acid) (TDTMP), Hexametilendiaminotetra (methylene phosphonic acid) (HDTMP), Diethylenetriaminepenta (methylene phosphonic acid) (DTPMP), Ethylenediaminetetraacetic acid (EDTA), Phosphonobutane tricarboxylic acid (PBTC), N-(phosphonomethyl) iminodiacetic acid (PMIDA), 2-Carboxy ethyl phosphonic acid (CEPA), 2-Hydroxy phosphono carboxylic acid (HPCA), Amino-tris (methylene phosphonic acid) (AMP), Sodium tripolyphosphate (STPP), Hydroxyethyl ethylene diaminne triacetic acid (HEDTA), Dihydroxy ethyl ethylene diamine diacetic acid, Diehylene triamine pentaacetic acid (DTPA), Triethylene tetramine hexaacetic acid (TTHA), Ethylene diamine di-hydroxyphenyl acetic acid (EDDHA), Ethylene diamine di-(2-hydroxy-5-sulphophenylacetic) acid (EDDHSA), Ethylene diamine di-hydroxy-methylphenylacetic acid (EDDHMA), Ethylene diamine di-(5-carboxy-2-hydroxyphenyl) acid (EDDCHA), Calcium disodium ethylene diamine tetraacetate (CaNa2EDTA), Nitrile triacetic acid (NTA), Propylene diamine tetraacetic acid (PDTA), Polyflavonoides, Sulfonates, Dimercaptosuccinic acid, Fulvic and humic acid, Lignosulphonic acid, Gluconic acid, Amino acids, Polysaccharides, Polyols, Glutamic acid, Citric, tartaric, ascorbic, malic, fumaric, lactic acid and combinations thereof.

19. The hygiene article according to claim 12, wherein said physical agent comprises ionones and wherein said ionones are selected from the group consisting of β-ionone, 1-(2,6,6-trimethyl-1-cyclohexenyl)pent-1-en-3-one; 4-(2,6,6trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)4-penten-3-one, (E)-4-(2,2-dimethyl-6-methylidenecyclohexyl)but-3-en-2-one and a mixture thereof.

20. The hygiene article according to claim 12, obtained by treating a topsheet, a backsheet, at least one layer disposed between the topsheet and the backsheet of the hygiene article, or a combination thereof with said odour control composition.

21. Method for manufacturing the hygiene article according to claim 12, comprising the steps of:
   a. providing a hygiene article comprising a liquid permeable topsheet, a liquid impermeable backsheet and at least one layer disposed between said liquid permeable topsheet and said liquid impermeable backsheet;
   b. treating the at least one layer, the liquid permeable topsheet, the liquid impermeable backsheet, or a combination thereof with an odour control composition consisting essentially of:
      an organic zinc salt;
      an anti-microbial agent comprising essential oil of thyme or thymol; and
      a chelating agent, a physical agent, or a combination thereof.

22. Method for manufacturing the hygiene article according to claim 12, comprising the steps of:
   a. treating a liquid permeable topsheet, a liquid impermeable backsheet, at least one layer, suitable for use in a hygiene article, or combinations thereof with an odour control composition consisting essentially of:
      an organic zinc salt;
      an anti-microbial agent comprising essential oil of thyme or thymol; and
      a chelating agent, a physical agent, or a combination thereof; and
   b. assembling the hygiene article by disposing the at least one layer between said liquid permeable topsheet and said liquid impermeable backsheet.

23. A method of controlling odour comprising administering the hygiene article of claim 12.

24. The method of claim 23, wherein the odour is caused by urine, menses, blood, blood components, vaginal secretions, sweat, or a combination thereof.

* * * * *